(12) United States Patent
Wilkerson

(10) Patent No.: US 7,205,376 B2
(45) Date of Patent: Apr. 17, 2007

(54) PROCESSES FOR THE PRODUCTION OF CUMENE, POLYETHERIMIDES, AND POLYCARBONATES

(75) Inventor: James Ralph Wilkerson, Harrisburg, IL (US)

(73) Assignee: General Electric Company, Schenectady, NY (US)

( * ) Notice: Subject to any disclaimer, the term of this patent is extended or adjusted under 35 U.S.C. 154(b) by 343 days.

(21) Appl. No.: 10/897,732

(22) Filed: Jul. 22, 2004

(65) Prior Publication Data

US 2006/0020047 A1 Jan. 26, 2006

Related U.S. Application Data

(60) Provisional application No. 60/567,850, filed on May 4, 2004.

(51) Int. Cl.
*C08F 6/00* (2006.01)
(52) U.S. Cl. ............. 528/196; 528/125; 528/198; 568/385; 585/467; 585/469
(58) Field of Classification Search ........... 528/125, 528/196, 198; 568/385; 585/467, 469
See application file for complete search history.

(56) References Cited

U.S. PATENT DOCUMENTS

| | | | |
|---|---|---|---|
| 2,577,768 A | 12/1951 | Joris | |
| 2,613,227 A | 10/1952 | Joris | |
| 2,619,509 A | 11/1952 | Joris | |
| 2,632,026 A | 3/1953 | Conner | |
| 2,632,774 A | 3/1953 | Conner et al. | |
| 2,689,936 A | 9/1954 | Kirsch et al. | |
| 3,169,121 A | 2/1965 | Goldberg | |
| 3,187,055 A | 6/1965 | Armstrong et al. | |
| 3,417,158 A | 12/1968 | Forry et al. | |
| 3,523,977 A | 8/1970 | Reni et al. | |
| 3,635,895 A | 1/1972 | Kramer | |
| 3,803,085 A | 4/1974 | Takehoshi et al. | |
| 3,847,867 A | 11/1974 | Heath et al. | |
| 3,850,885 A | 11/1974 | Takekoshi et al. | |
| 3,852,242 A | 12/1974 | White | |
| 3,855,178 A | 12/1974 | White et al. | |
| 3,905,942 A | 9/1975 | Takekoshi et al. | |

(Continued)

FOREIGN PATENT DOCUMENTS

EP 0 839 786 B1 7/1997

(Continued)

OTHER PUBLICATIONS

AU625001; Jun. 25, 1992; Synthesis of Methanol From Natural Gas ;English Abstract; only one page.

(Continued)

*Primary Examiner*—Terressa Boykin

(57) ABSTRACT

A method for the manufacture of polycarbonate by combining methane and inlet water to produce methanol, converting the methanol to propylene, gasoline aromatics, and gasoline olefins, converting the propylene and gasoline olefins to hydrogen, first benzene, and toluene, reacting the first benzene with propylene to form cumene, reacting the cumene with oxygen to form cumene hydroperoxide, cleaving the cumene hydroperoxide to produce acetone and phenol, reacting the phenol, additional phenol, and acetone to produce a dihydric aromatic compound, and reacting the dihydric aromatic compound with a carbonate precursor to form polycarbonate.

18 Claims, 5 Drawing Sheets

U.S. PATENT DOCUMENTS

| | | | |
|---|---|---|---|
| 3,907,901 A | 9/1975 | Feder et al. |
| 3,933,921 A | 1/1976 | Suda et al. |
| 3,963,794 A | 6/1976 | Myers et al. |
| 3,972,902 A | 8/1976 | Heath et al. |
| 3,983,093 A | 9/1976 | Williams, III et al. |
| 4,001,184 A | 1/1977 | Scott |
| 4,008,290 A | 2/1977 | Ward |
| 4,025,576 A | 5/1977 | Chang et al. |
| 4,051,191 A | 9/1977 | Ward |
| 4,079,095 A | 3/1978 | Givens et al. |
| 4,153,635 A | 5/1979 | Wu et al. |
| 4,192,952 A | 3/1980 | Stueben |
| 4,199,437 A | 4/1980 | Courty et al. |
| 4,217,438 A | 8/1980 | Brunelle et al. |
| 4,283,568 A | 8/1981 | Pujado |
| 4,308,128 A | 12/1981 | Cummings |
| 4,329,514 A | 5/1982 | van der Weijst et al. |
| 4,343,957 A | 8/1982 | Sartorio et al. |
| 4,395,495 A | 7/1983 | Cummings |
| 4,406,699 A | 9/1983 | Beck et al. |
| 4,407,973 A | 10/1983 | van Dijk et al. |
| 4,443,591 A | 4/1984 | Schmidt et al. |
| 4,455,410 A | 6/1984 | Giles, Jr. |
| 4,487,896 A | 12/1984 | Mark et al. |
| 4,528,412 A | 7/1985 | Steacy |
| 4,533,780 A | 8/1985 | Maffia |
| 4,542,252 A | 9/1985 | Graziani et al. |
| 4,618,732 A | 10/1986 | Gesser et al. |
| 4,677,235 A | 6/1987 | Mowry |
| 4,806,699 A | 2/1989 | Smith et al. |
| 4,806,700 A | 2/1989 | Martindale |
| 5,120,902 A | 6/1992 | Tagamolila et al. |
| 5,220,103 A | 6/1993 | Tagamolila et al. |
| 5,229,482 A | 7/1993 | Brunelle |
| 5,258,563 A | 11/1993 | Gosling et al. |
| 5,430,200 A | 7/1995 | Hood |
| 5,434,326 A | 7/1995 | Gajda et al. |
| 5,496,859 A | 3/1996 | Fong et al. |
| 5,530,166 A | 6/1996 | Zakoshansky et al. |
| 5,569,791 A | 10/1996 | Hammerman et al. |
| 5,767,165 A | 6/1998 | Steinberg et al. |
| 5,767,322 A | 6/1998 | Zakoshansky et al. |
| 5,908,962 A | 6/1999 | Gopinathan et al. |
| 6,077,977 A | 6/2000 | Gopinathan et al. |
| 6,137,017 A | 10/2000 | Stauffer |
| 6,465,695 B1 | 10/2002 | Fulmer et al. |
| 6,506,954 B1 | 1/2003 | Brown et al. |
| 6,620,974 B2 | 9/2003 | Fulmer et al. |
| 6,632,971 B2 | 10/2003 | Brown et al. |
| 6,635,789 B2 | 10/2003 | Fulmer et al. |
| 2004/0054242 A1 | 3/2004 | Brown et al. |
| 2004/0059162 A1 | 3/2004 | Dyckman et al. |
| 2004/0260134 A1* | 12/2004 | Tsuji et al. ............ 585/469 |

FOREIGN PATENT DOCUMENTS

| | | |
|---|---|---|
| GB | 2 237 287 A | 5/1991 |
| WO | WO 01/07385 A1 | 2/2001 |
| WO | WO 2004/018089 A1 | 3/2004 |

OTHER PUBLICATIONS

CA2213025; Apr. 24, 1998; Process of Producing Methanol From Natural Gas; English Abstract; only one page.

Kirk-Othmer: "Encyclopedia of Chemical Technology; vol. 4"; 1992; Wiley Interscience Publication; p. 590-592 and p. 598, 603-604(XP002336149).

Chang, C.D.: "The New Zealand Gas-to-Gasoline Plant: An Engineering Tour de Force"; Catalysis Today, Elsevier, vol. 13, No. 1, 1992, pp. 103-111 (XP009050104).

Doolan, P.C. et al: "Make Aromatics from LPG"; Hydrocarbon Processing, Gulf Publishing Co.; Houston, US, vol. 68, No. 9, Sep. 1989; pp. 72-74, 76, ISSN: 0018-8190, Figures 1,2 (XP001206932).

"Ullmann's Encyclopedia of Industrial Chemistry, 6$^{th}$ edition, vol. 4"; 2003, Wiley-VCH, p. 725-729 (XP002336150).

Anonymous: "Q-Max Process"; Internet Article, 'Online!; Apr. 14, 2004; Retrieved from the Internet: URL:http://web.archive.org/web/02040414155328 http://www.uop.com/objects/31%200_MAX.pdf> 'retrieved on Jul. 5, 2005!; paragraph 'Commercial.Experience! figures (XP002336145).

"Ullmann's Encyclopedia of Industrial Chemistry, 6$^{th}$ edition, vol. 28"; 2003, Wiley-VCH, p. 353-354 (XP002336151).

European Search Report; International Application No. PCT/US2005/013719; Applicant's File Reference: 08CL 139925; International Filing Date: Apr. 22, 2005; Date of Mailing: Aug. 4, 2005.

USSR Author's Certificate 567723, published on Sep. 9, 1977 in Bulletin of Inventions No. 29.

Harald Koempel et al., Methanol to Propylene—MTP, An economical route to dedicated propylene, 2nd ICIS-LOR World Olefins Conference, Amsterdam, Feb. 11-12, 2002, mg engineering, Lurgi Oel, Gas, Chemie, pp. 1-7 and Table p. 1.

Klaus Weissermel et al., Industrial Organic Chemistry, Third Completely Revised Edition, VCH, pp. 312-324, 342-343, 353-355 and 358-359.

UOP, Aromatics and Derivatives, Q-Max Process, 2 pages.

UOP, Process Technology and Equipment, UOP/HYDRO MTO Process Methanol to Olefins Conversion, 2 pages.

UOP, Aromatics and Derivatives, Cyclar Process, pp. 1-3.

US 4,421,907, 12/1983, Schmidt et al. (withdrawn)

\* cited by examiner

US 7,205,376 B2

PROCESSES FOR THE PRODUCTION OF CUMENE, POLYETHERIMIDES, AND POLYCARBONATES

CROSS REFERENCE TO RELATED APPLICATIONS

The present application claims priority to U.S. Provisional Application No. 60/567,850, filed May 4, 2004.

BACKGROUND

Many important industrial chemicals are derived from petroleum, and their cost and availability are related to the cost and availability of crude oil and the accessibility of appropriate processing facilities. For example, benzene is produced mostly from oil refinery streams including catalytic reformate and pyrolysis gasoline, and propylene is typically produced from steam cracking of various hydrocarbons and from refinery cracking operations. The value of feedstock used for these processes is often tied to a fuel value or other volatile indicator. Benzene, toluene, and xylenes (BTX) are valuable feedstocks for numerous chemical processes.

There is a constant drive to reduce the cost of these feedstocks. Methods of reducing the costs and increasing the availability of benzene, toluene, etc., would be advantageous.

BRIEF DESCRIPTION

Disclosed herein are methods of making polycarbonate, polyetherimide, benzene, bisphenol-A, and cumene. In one embodiment, the method for the manufacture of polycarbonate comprises: combining methane and inlet water to produce methanol, converting the methanol to propylene, gasoline aromatics, and gasoline olefins, converting the propylene and gasoline olefins to hydrogen, first benzene, and toluene, reacting the first benzene with propylene to form cumene, reacting the cumene with oxygen to form cumene hydroperoxide, cleaving the cumene hydroperoxide to produce acetone and phenol, reacting the phenol and acetone to produce a dihydric aromatic compound, and reacting the dihydric aromatic compound with a carbonate precursor to form polycarbonate.

In one embodiment, the method for the manufacture of polyetherimide comprises: combining methane and inlet water to produce methanol, converting the methanol to propylene, gasoline aromatics, and gasoline olefins, converting the propylene and gasoline olefins to hydrogen, first benzene, and toluene, reacting the first benzene with propylene to form cumene, reacting the cumene with oxygen to form cumene hydroperoxide, cleaving the cumene hydroperoxide to produce acetone and phenol, reacting the phenol and acetone to produce a dihydric aromatic compound, reacting the dihydric aromatic compound with a base to form a dihydric aromatic salt, reacting the dihydric aromatic salt with a nitro substituted phenyl dinitrile to form an aromatic bis(ether anhydride) and reacting the aromatic bis(ether anhydride) with a diamine to form polyetherimide.

In one embodiment, the method for the manufacture of polyetherimide comprises: combining methane and inlet water to produce methanol, converting the methanol to propylene, gasoline aromatics, and gasoline olefins, converting the propylene and gasoline olefins to hydrogen, first benzene, and toluene, reacting the first benzene with propylene to form cumene, reacting the cumene with oxygen to form cumene hydroperoxide, cleaving the cumene hydroperoxide to produce acetone and phenol, reacting the phenol and acetone to produce a dihydric aromatic compound, reacting the dihydric aromatic compound with a base to form a dihydric aromatic salt, reacting the dihydric aromatic salt with a bis(halophthalimide) to form polyetherimide.

In one embodiment, the method for the manufacture of cumene comprises: combining methane and inlet water to produce methanol, converting the methanol to propylene, gasoline aromatics, and gasoline olefins, converting the propylene and gasoline olefins to hydrogen, first benzene, and toluene, and reacting the first benzene with propylene to form cumene.

The above described and other features are exemplified by the following figures and detailed description.

BRIEF DESCRIPTION OF THE FIGURES

Referring now to the figures, which are exemplary embodiments, and wherein the like elements are numbered alike.

DETAILED DESCRIPTION

Figure 1:
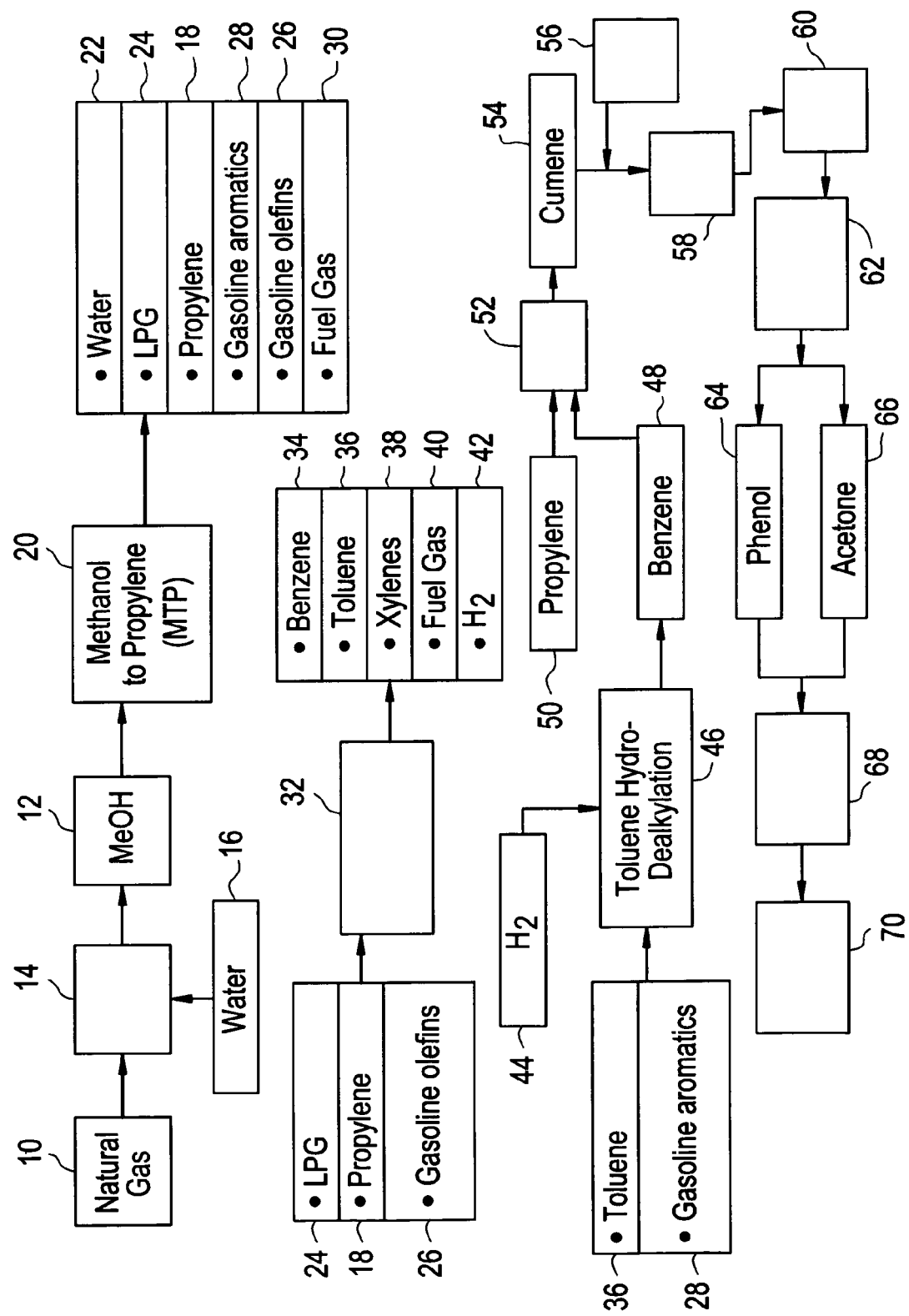
FIG. 1 is a schematic representation of one embodiment of a process for the production of cumene from natural gas (methane)

The process described herein provides a source and method of production of benzene, toluene, xylene, and other basic aromatic compounds, aromatic derivatives thereof (such as phenol and bisphenol A), and polycarbonates made therefrom, as well as other chemical products derived from benzene, toluene or xylenes, etc. This process provides an alternative to starting with petroleum base stock, i.e., crude oil. The process converts methane to methanol, methanol to propylene, propylene to benzene, benzene to phenol, and, optionally, phenol to polycarbonate. The methane may be provided in a methane source, e.g., natural gas, coal bed methane, etc. It is noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced item. Additionally, all ranges disclosed herein are inclusive and combinable (e.g., ranges of "up to about 25 wt %, with about 5 wt % to about 20 wt % desired," is inclusive of the endpoints and all intermediate values of the ranges of "about 5 wt % to about 25 wt %," etc.).

Processes leading to the production of benzene from a methane source include a first process that comprises converting methane source, e.g., methane in natural gas 10, to methanol (MeOH) 12 in a methanol generation process 14 by reaction with water 16. The methanol 12 from the methanol generation process is then used as feedstock for a process for the manufacture of propylene 18 (i.e., a methanol-to-propylene process 20). The methanol-to-propylene process 20 generates water 22, liquefiable petroleum gas (LPG) 24, gasoline olefins 26, gasoline aromatics 28 and fuel gas 30 in addition to the propylene 18. The water 22 can be recycled into the methanol-to-propylene process 20.

The LPG 24, propylene 18 and gasoline olefins 26 (which may comprise $C_3$ and/or $C_4$ olefins) from the methanol-to-propylene process 20 are then used as a feedstock for a production of aromatics process 32 that produces aromatic species, e.g., benzene 34, toluene 36, and xylenes 38 (which together comprise BTX), fuel gases 40, and hydrogen 42. Optionally the toluene 36 and gasoline aromatics 28 from the methanol-to-propylene process 20 are further processed with hydrogen 44 (which may comprise hydrogen 42 from process 32) to yield additional benzene 48, e.g., in a toluene hydro-dealkylation process 46. The benzene 48 and/or benzene 34 can then be reacted with propylene 50 and/or propylene 18 from the methanol-to-propylene process 20 in an alkylation process 52 to form cumene 54.

Cumene has a variety of uses. For example, cumene 54 can be reacted with oxygen 56 in an oxidation process 58 to yield cumene hydroperoxide 60, from which phenol 64 and acetone 66 can be derived, e.g., in an acidic cleavage process 62. The phenol 64 and acetone 66 can be reacted in a process 68, e.g., a condensation process, to form a dihydric aromatic compound 70 (e.g., bisphenol A (BPA)). The BPA or other dihydric aromatic compound can then be used in the production of polymeric materials such as polycarbonate, polyetherimide, and the like.

This process provides a useful alternative to the use of petroleum-derived BTX, propylene, etc, especially in locations where "stranded" natural gas (i.e., natural gas reserves that are not near facilities for gas recovery and processing), is reported available at very competitive prices. At such locations, natural gas is often merely flared off, and so would be available at very low cost.

A general schematic representation of a process for the production of cumene from natural gas (methane) is set forth in FIG. 1. One methanol generation process comprises generating synthesis gas (syngas) from the natural gas, as an intermediate. The synthesis gas can be generated using steam methane reforming, partial oxidation or gasification, or a combined reforming or autothermal reforming process.

Steam methane reforming is the catalytic reaction of natural gas with steam to produce a synthesis gas or "syngas", which includes $H_2$, $CO_2$, CO, $CH_4$, and $H_2O$, with an $H_2$ to CO molar ratio of about 3:1 or higher. The steam methane reformation reaction is endothermic. Therefore, external heat is required. For example, the natural gas and steam ("inlet water") are fed into alloy tubes that contain a nickel based catalyst for the reforming reaction. The catalyst tubes are placed inside a refractory lined structure. A portion of the natural gas can be used as fuel to provide the heat required for the reaction:

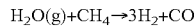

$$H_2O(g)+CH_4 \rightarrow 3H_2+CO$$

Partial oxidation or gasification is a non-catalytic reaction of natural gas with oxygen under controlled oxygen conditions. The reaction is exothermic as shown in the following reaction:

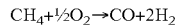

$$CH_4+\tfrac{1}{2}O_2 \rightarrow CO+2H_2$$

The partial oxidation process can be operated at high pressure, e.g., 200 to 2,000 psig, to minimize or eliminate the syngas compression needed to reach the desired elevated pressure suitable for methanol production. However, the syngas produced from the partial oxidation process has a lower $H_2$:CO ratio than syngas from steam reforming, and little or no $CH_4$ content. As a result, external hydrogen can be employed to meet the methanol syngas requirements.

A combined reforming process uses a combination of steam methane reforming, often referred to as "primary reforming", in combination with oxygenated catalytic reforming. In one embodiment, a portion of the natural gas feedstock is fed to the primary reformer and the effluent is blended with the balance of the natural gas and oxygen prior to entering a secondary reformer.

In one embodiment, natural gas can be partially oxidized in a gasifier to produce hot pressurized syngas. The hot gasifier syngas can be passed for indirect heat exchange through a steam reforming catalytic reactor where an endothermic reforming reaction is conducted with a gaseous feedstock and steam to produce a reformer syngas. A portion of the reforming syngas can be recycled as feed to the gasifier while the remaining portion is combined with partially cooled gasifier syngas exiting the catalytic reactor to form a stoichiometric ratioed syngas. The ratio adjusted syngas then enters a methanol synthesis unit at conditions to convert it to methanol. This process can be accomplished with little or no external compression. Optionally, prior to entering the methanol synthesis unit, the ratio adjusted synthesis gas can be cooled to a desired operating temperature in a series of heat exchangers and/or steam generators for optimal heat recovery.

In one embodiment, a stoichiometric ratioed syngas can be supplied to a methanol synthesis unit generally conforming to the following specifications:

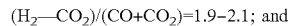

$(H_2-CO_2)/(CO+CO_2)=1.9-2.1$; and

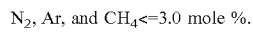

$N_2$, Ar, and $CH_4 \leq 3.0$ mole %.

The methanol syngas is fed to a methanol synthesis reactor, at the desired pressure (e.g., 700 to 2,000 pounds per square inch gauge (psig)), depending upon the process employed. The methanol syngas then reacts under the influence of a catalyst to form methanol. The reaction is exothermic. Therefore, heat removal is ordinarily desirable. The raw or impure methanol can then be condensed and purified to remove impurities such as higher alcohols, including ethanol, propanol, and the like, while the uncondensed vapor phase (comprising unreacted methanol syngas) can be recycled to the feed.

The methanol can be converted into propylene by various methods. Processes for converting the methanol can employ aluminosilicate(s), molecular sieve(s), and/or zeolites(s), e.g., zeolites(s) with coke thereon (e.g., to selectivity produce light olefins and minimize the formation of $C_{5+}$ byproducts), silico aluminophosphates. For example, the H-SAPO-34 and Ni-SAPO-34 materials can be used for the conversion of methanol to light olefins, such as ethylene, propene, and butene. The microporous silicoaluminophosphate H-SAPO-18 (AEI, 8-ring pores) has also been applied as a catalyst for the production of propylene from methanol. To facilitate production of propylene from methanol, the reaction stages that comprise a zeolite can be disposed vertically on top of each other in an upright reaction container, with heat exchanger(s) mounted between the reaction stages. One catalyst for the methanol conversion may be a metalloaluminophosphate molecular sieve having the empirical formula $(El_xAl_yP_z)O_2$ where El is a metal such as silicon or magnesium and "x", "y" and "z" are the mole fractions.

One methanol-to-propylene process comprises a pre-reaction stage that comprises a catalyst (e.g., an aluminum oxide catalyst) for forming a pre-reaction mixture comprising methanol vapor, dimethyl ether vapor, and water vapor. In one embodiment of this process, the methanol can be converted, over a catalyst, to a pre-reaction equilibrium mixture of dimethyl ether, unreacted methanol, and steam. Several reaction stages may then be employed, e.g., with a zeolite, for reacting the pre-reaction mixture to yield a reaction mixture containing propylene and other light olefins. There can be heat exchanger(s) disposed between the reaction stages for cooling the reaction mixture. Additionally, one or more heat exchangers can be disposed downstream of the last reaction stage for further cooling of the reaction mixture. In addition to propylene, a methanol to propylene system may produce significant amounts of liquefiable petroleum gas, gasoline aromatics, gasoline olefins, and fuel gas.

One such system includes a device for separating the reaction mixture into a gas phase and a liquid phase containing mostly water, a compressor for compressing the gas phase, a device for separating the mixture formed during compression into a gas phase containing hydrocarbons and a liquid phase containing dimethyl ether, water, and methanol, and a device for separating the phase containing hydrocarbons into propylene and other hydrocarbons.

The conversion of methanol to light olefins is effected by contacting the methanol with the catalyst at conversion conditions, thereby forming the desired light olefins. The methanol can be in the liquid or vapor phase with the vapor phase more desirable. Contacting the methanol with the catalyst can be done in a continuous mode or a batch mode with a continuous mode being more desirable. The amount of time that the methanol is in contact with the catalyst is sufficient to convert the methanol to the desired light olefin products. When the process is carried out in a batch process, the contact time varies, e.g., can be 0.001 hour (hr) to 1 hr, or, more specifically, 0.01 hr to 1.0 hr. Longer contact times are used at lower temperatures, while shorter times are used at higher temperatures. Further, when the process is carried out in a continuous mode, the weight hourly space velocity (WHSV) based on methanol can be, e.g., 1 $hr^{-1}$ to 1,000 $hr^{-1}$, and specifically, e.g., 1 $hr^{-1}$ to 100 $hr^{-1}$. Generally, the process can be carried out at elevated temperatures in order to form light olefins at a fast enough rate to render it feasible for commercial production, e.g., temperatures of 300° C. to 600° C., more specifically, 400° C. to 550° C. The process may be carried out over a wide range of pressures, including autogenous pressure. Thus, the pressure can be about 0 kilopascals (kPa; 0 psig) to about 1,724 kPa (250 psig), and specifically about 34 kPa (5 psig) to about 345 kPa (50 psig).

Optionally, the methanol feedstock may be diluted with a diluent in order to more efficiently convert the methanol to olefins. Examples of the diluents which may be used include helium, argon, nitrogen, carbon monoxide, carbon dioxide, hydrogen, steam, paraffinic hydrocarbons, e.g., methane, aromatic hydrocarbons, e.g., benzene, toluene and mixtures comprising at least one of the foregoing diluents. The amount of diluent used can vary considerably, e.g., the diluent may comprise about 5 to about 90 mole percent (mol %) of the feedstock, more specifically, about 25 mol % to about 75 mol %, based upon the total moles of material in the feedstock.

The actual configuration of the reaction zone may be a single reaction zone or a number of zones arranged in series or parallel, with one or more catalysts employed therein. Optionally, a fixed bed, and/or a dynamic bed system (e.g., fluidized bed, moving bed, or the like), may be used, wherein a dynamic system could be employed to facilitate regeneration of the catalyst as desired. For example, the catalyst can be continuously introduced as a moving bed to a regeneration zone where it can be regenerated, e.g., such as by oxidation in an oxygen containing atmosphere to remove carbonaceous materials.

Figure 2:
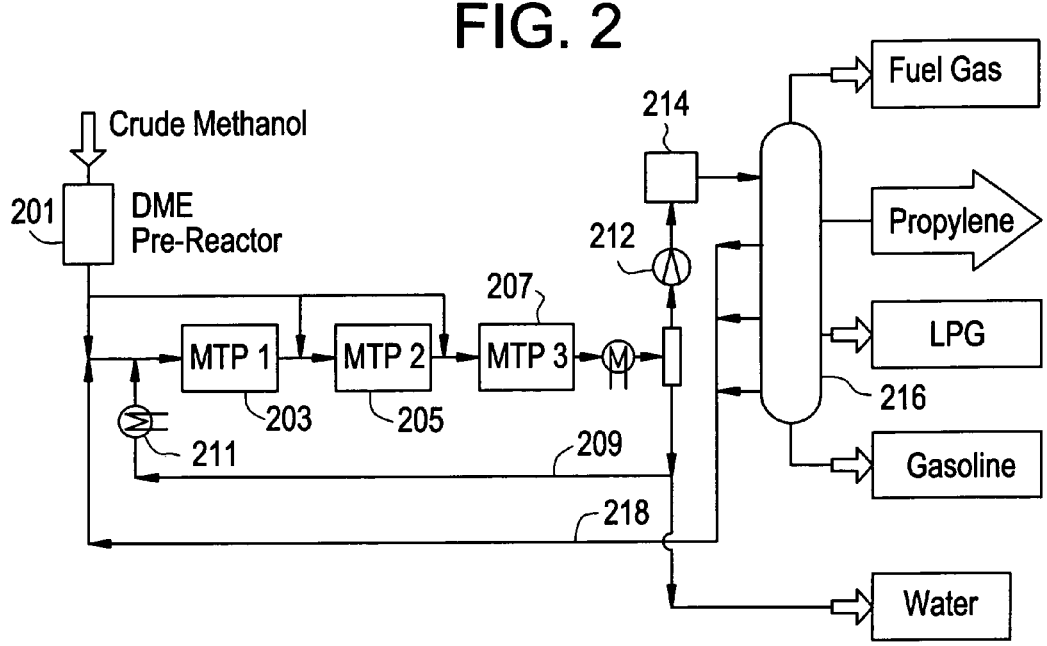
FIG. 2 is a simple schematic representation of one embodiment of a process for the conversion of methanol to propylene.

One embodiment of a method for the production of light olefins from methanol is shown schematically in FIG. 2. The methanol feed can be sent to an adiabatic DME pre-reactor 201 where methanol is converted to DME (di-methyl ether) and water. Optionally, a high-activity, high-selectivity catalyst is used to nearly achieve thermodynamic equilibrium. The methanol/water/DME stream and steam are routed to a first reactor 203. The majority of the methanol and DME may be converted to fuel gas, propylene, LPG, gasoline, and water, in the first reactor 203, with propylene as the predominant hydrocarbon product. Additional reactions can proceed with optional subsequent reactors (e.g., second reactor 205 and third reactor 207). The reaction conditions in the reactors (203, 205, 207) can be chosen to maximum overall propylene yield. The product mixture can then be cooled and the product gas, organic liquid, and water separated in a separator 210. The product gas can be compressed 212 and traces of water, $CO_2$, and DME can be removed. The cleaned gas can then be further processed 214 to yield chemical- or polymer-grade propylene fuel gas, LPG, gasoline and water 216. Several olefin-containing streams can optionally be sent back 218 to the main synthesis loop (e.g., to any of the reactors) as additional propylene source material. To avoid accumulation of inert materials in the loop, a purge can be used for light-ends and the $C_4/C_5$ cut. Water can be recycled 209 to steam generation 211, while excess water can be purged and/or, optionally, the water can be reverted to the methanol generation process 14 for reaction with methane to generate syngas for the production of methanol.

Figure 3:
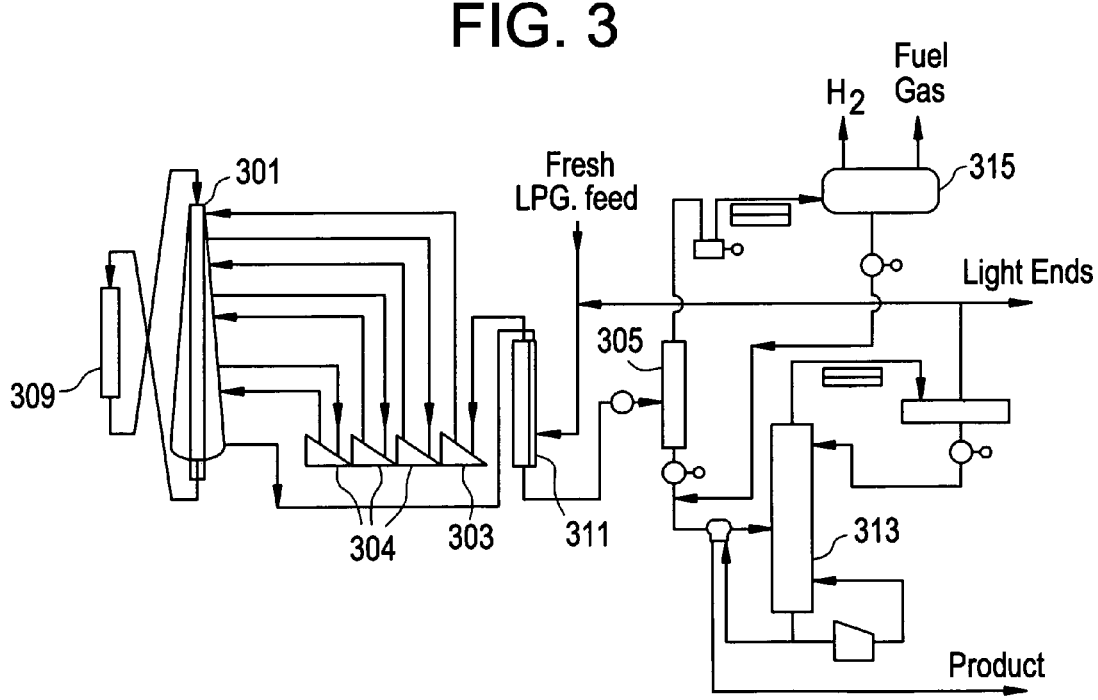
FIG. 3 is a simple schematic representation of one embodiment of a process for conversion of light olefins to aromatics.

The propylene, and optionally the LPG and gasoline olefins from the methanol-to-propylene process, may then be used as the feedstock for a process for producing BTX (benzene, toluene, and xylene) aromatics, fuel gases, and hydrogen. One such process is illustrated schematically in FIG. 3.

The process for generating aromatics, which may be described as dehydrocyclodimerization, is thermodynamically favored at temperatures greater than or equal to 425° C. (800° F.), with the dehydrogenation of light paraffins (propane and butanes) to olefins being the rate limiting step. Once formed, the highly reactive olefins oligomerize to form larger intermediates, which then rapidly cyclize. These reactions, dehydrogenation, oligomerization, and cyclization, can all be acid catalyzed, e.g., using a solid acid catalyst such as a zeolite. The shape selectivity of a zeolite component of the catalyst can promote the cyclization reaction, limiting the size of the rings formed. Optionally, a gallium-loaded zeolite catalyst can be employed.

Optionally, the final reaction step can be the dehydrogenation of the naphthenes to their corresponding aromatics. Heavier paraffins such as pentanes can also be included in the feed. Although the reaction sequence involves exothermic steps, the preponderance of dehydrogenation reactions results in an endothermic overall reaction. This is easily understood from the fact that five moles of hydrogen are produced for every mole of aromatic formed from propane or butane.

For example, the process can use: (1) a reactor section, e.g., comprising a radial-flow reactor stack, combined feed exchanger, charge heater, and/or interheaters, (2) a catalyst regenerator section, e.g., comprising a regenerator stack and catalyst transfer system, and (3) a product recovery section, e.g., comprising product separators, compressors, strippers, and/or gas recovery equipment.

The flow scheme can comprise combining fresh feed and recycle in a combined feed exchanger 311 and heat exchanging against reactor effluent. The combined feed is then raised to reaction temperature in the charge heater 303 and sent to the reactor section. The reactor section may comprise multiple (e.g., four) adiabatic, radial-flow reactors arranged in one or more vertical reactor stacks 301 such that catalyst flows by gravity down the stack, while the charge flows radially across the annular catalyst beds. Between each reactor, the charge can be reheated to reaction temperature in an interheater 304. The effluent from the last reactor can be passed through exchanger 311 for heat exchange and may then be split into vapor and liquid products in a separator 305. The liquid can be sent to a stripper 313 where light saturates are removed from the $C_{6+}$ aromatic product, which may then be collected after optional heat exhange with the liquid product feed to the stripper. The light saturates can be recycled into the feed stream. Vapor from the separator can be compressed and sent to a gas recovery section 315 (e.g., a cryogenic unit), for separation into a hydrogen product stream, a fuel gas stream of light saturates, and a recycle stream of unconverted LPG.

Over time coke can build up on the catalyst under reaction conditions. The partially deactivated catalyst can be withdrawn (e.g., continually or periodically) from the bottom of the reactor stack 301 and transferred to the regenerator 309 for regeneration. The catalyst flows down through the regenerator stack 301 where the accumulated carbon is burned off. Regenerated catalyst is lifted, e.g., with hydrogen, to the top of the reactor stack 301. Because the reactor and regenerator sections are separate, each can operate at its own optimum conditions. In addition, the regenerator section can be temporarily shut down for maintenance without affecting the operation of the reactor and product recovery sections.

The principal operating variables in a process for producing aromatics (e.g., BTX) from propylene, LPG and light olefins, are feedstock composition, pressure, space velocity, and temperature. Desirably, the temperature is high enough to facilitate the conversion of reaction intermediates in order to reduce the presence of nonaromatic impurities in the liquid product, but low enough to reduce nonselective thermal reactions to acceptable levels. Additionally, space velocity is desirably optimized against conversion within this temperature range to obtain high product yields with minimum operating costs. Reaction pressure has a big impact on process performance and can be chosen based upon yield and cost type factors. For example, a low pressure design can be employed to enhance aromatic yield, while a high-pressure design is employed to reduce the amount of catalyst employed (e.g., can use about half the catalyst as the low-pressure design) and is attractive where minimum investment and operating costs are the overriding considerations.

The major liquid products from the process are benzene, toluene, xylenes, and heavier aromatics. Petrochemical grade toluene and xylenes can be obtained by fractionation alone, without the need for subsequent extraction. The by-product light ends contain substantial amounts of hydrogen, which may be recovered in several different ways, depending on the purity desired. An absorber/stripper system can produce a 65 mol % hydrogen product stream; a cold box can produce a 95 mol % hydrogen product stream; an absorber-stripper system combined with a pressure swing adsorption (PSA) unit can produce a 99 mol % hydrogen product stream; and a cold box combined with a PSA unit can produce a greater than or equal to 99 mol % hydrogen product stream, if desired; wherein the mole percentage is based upon the total moles in the product stream.

Optionally, additional benzene may be obtained from the toluene, xylenes, gasoline aromatics generated in the production of propylene from methanol, etc., produced above, by the method of toluene hydrodealkylation under catalytic and/or thermal conditions. Under this process, the toluene, xylene and/or gasoline aromatics are mixed with a hydrogen stream and then passed through a vessel that contains a catalyst. In one such process, the temperature in this vessel is about 500° C. to about 595° C., and the pressure is about 4 megaPascals (Mpa) to about 6 MPa. The products that are leaving the generator pass through a separator, where the unreacted hydrogen is removed and optionally recycled to the feed. Methane can be separated from the benzene product with fractionation.

Benzene from the production of BTX and/or from toluene hydrodealkylation can then be used to produce cumene (isopropylbenzene). Cumene can be obtained from benzene by alkylation with propylene, optionally including some propylene 18 (FIG. 1) obtained from the process of generating propylene, etc., from methanol 20. Some possible aromatic-olefin alkylation catalysts that can be used in catalytic alkylation of benzene include: Friedel-Crafts catalysts in either liquid or solid supported form (e.g., sulfuric acid, phosphoric acid, hydrofluoric acid, aluminum chloride, and the like); solid granular catalysts (such as clay(s), zeolites(s), amorphous material(s), and the like); as well as combinations comprising at least one of the foregoing.

A transalkylation reaction zone may be added to an alkylation zone to enable higher alkylation conversion through reaction of the resulting undesired polyalkylaromatics into desired monoalkylaromatic compounds. The transalkylation catalyst may be the same or a different composition than the alkylation catalyst. The alkylation may be effected in a variety of processing schemes employing one or more alkylation reaction zone(s), transalkylation reaction zone(s), and separation zone(s), with various product, feed, and intermediate-product recycles.

The alkylation reaction is exothermic in nature and the temperature within the reactor tends to increase at a rapid rate. This increase in temperature caused tends to increase the production of cumene bottoms products. The temperature rise may be controlled, for example, by catalyzing the reaction in multiple separate zones and/or employing a quenching medium between the successive alkylation zones. This quenching has served to control the temperature at which the reaction mixture enters each successive zone and thus the temperature rise throughout each zone. The temperature rise from the inlet to the outlet of the reactor can also be controlled by controlling the molar excess of benzene charged to the reactor, with the benzene acting as a heat sink to absorb heat released by the alkylation reaction. Accordingly, increasing the molar excess of benzene charged to the reactor, with a corresponding dilution of the propylene reactant therein, not only provides more aromatic sites subject to alkylation and a resulting reduction in oligomers and over alkylated by-products, but also reduces the formation of undesirable by-products resulting from an excessive temperature rise across an alkylation zone or zones.

Figure 4:
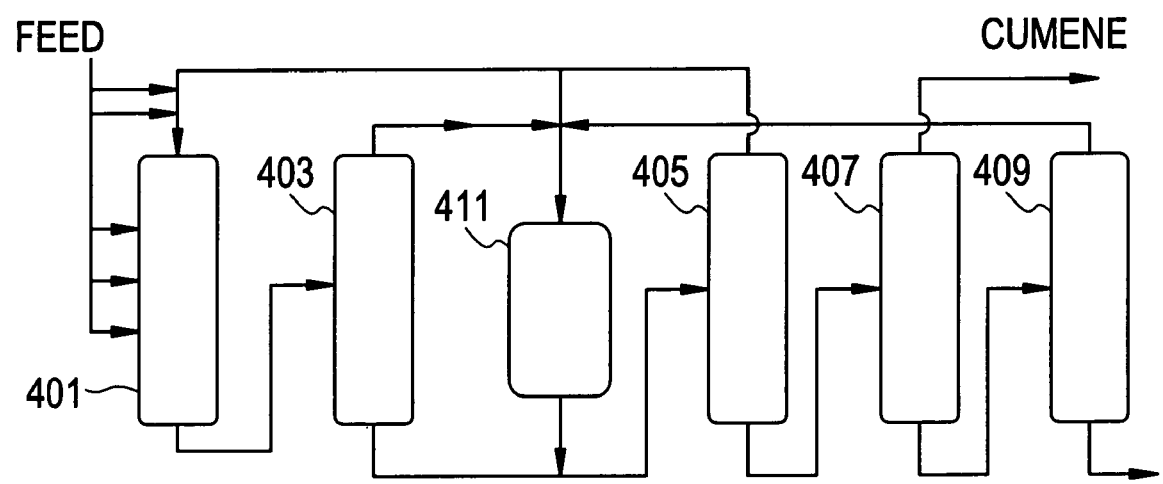
FIG. 4 is a simple schematic representation of one embodiment of a process for the production of cumene.

In one such process depicted schematically in FIG. 4, liquid benzene and liquid propylene are charged into a reactor 401 and reacted therein in alkylation zone(s) in contact with an alkylation catalyst. To reduce the production of dialkylated products of benzene, it has been the practice to maintain a molar ratio of benzene to propylene throughout the reaction zone at about 4:1 to about 16:1 or, more specifically, about 5:1 to about 10:1, and even more specifically, about 8:1.

Effluent from the alkylation reactor is sent to a depropanizer column 403, which removes the propane that entered the unit with the propylene feed, along with any excess water which may have accompanied the feeds. The depropanizer column bottoms are sent to a benzene column 405 where benzene is collected overhead and recycled. Benzene column bottoms are sent to the cumene column 407 where cumene product is recovered overhead. The bottoms from the cumene column, containing mostly diisopropylbenzene (DIPB), are sent to a DIPB column 409 where DIPB is recovered and recycled to a transalkylation reactor 411. The bottoms from the DIPB column consists of a small stream of heavy aromatic by-products which are normally blended into fuel oil. Steam or hot oil provides the heat for the product fractionation section. A portion of the recycle benzene from the top of the benzene column 405 is combined with the recycle DIPB from the overhead of the DIPB column 409 and sent to the transalkylation reactor 411. In the transalkylation reactor 411, DIPB and benzene are converted to additional cumene. The effluent from the transalkylation reactor is then sent to the benzene column.

As described above, the cumene can then be converted to cumene hydroperoxide (CHP) by the addition of oxygen, wherein the cumene hydroperoxide can, in turn, be cleaved to produce phenol and acetone. This phenol and acetone can then be employed in the production of a bisphenol (e.g., bisphenol-A).

The acid catalyzed reaction of phenol with specific aldehyde or ketone yields a 4,4'-bisphenol with specific groups derived from the aldehyde or the ketone connecting the two phenolic rings. In particular when phenol is reacted with acetone, the dihydric aromatic 4,4'(hydroxyphenyl)propane-2, hereafter known as bisphenol-A or BPA is formed. Therefore, to obtain BPA the phenol may be reacted with the acetone obtained from the treatment of cumene. By using a ketone other than or in addition to acetone, other bisphenols may be obtained as well.

Bisphenols such as bisphenol-A (BPA) are useful as a building block of polycarbonate, polyetherimide, and other plastics that can be used to make numerous consumer products. BPA is also used in epoxy resins, in the plastic lining of some food cans, in some dental sealants, and as an additive in other consumer products. BPA also has utility in the manufacture of polyarylates and copolyestercarbonates.

As used herein, the terms "polycarbonate" and "polycarbonate resin" means compositions having repeating structural carbonate units of the formula (1):

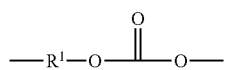
(1)

in which at least about 60 percent of the total number of $R^1$ groups are aromatic organic radicals and the balance thereof are aliphatic, alicyclic, or aromatic radicals. Preferably, each $R^1$ is an aromatic organic radical and, more preferably, a radical of the formula (2):

wherein each of $A^1$ and $A^2$ is a monocyclic divalent aryl radical and $Y^1$ is a bridging radical having one or two atoms that separate $A^1$ from $A^1$. In an exemplary embodiment, one atom separates $A^1$ from $A^2$. Illustrative non-limiting examples of radicals of this type are —O—, —S—, —S(O)—, —S(O$_2$)—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ is preferably a hydrocarbon group or a saturated hydrocarbon group such as methylene, cyclohexylidene, or isopropylidene.

Polycarbonates may be produced by the interfacial reaction of dihydroxy compounds having the formula HO—$R^1$—OH, which includes dihydroxy compounds of formula (3)

wherein $Y^1$, $A^1$ and $A^2$ are as described above. Also included are bisphenol compounds of general formula (4):

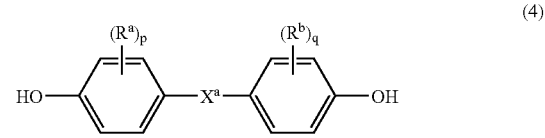

wherein $R^a$ and $R^b$ each represent a halogen atom or a monovalent hydrocarbon group and may be the same or different; p and q are each independently integers of 0 to 4; and $X^a$ represents one of the groups of formula (5):

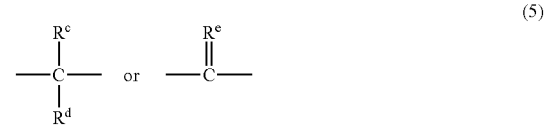

wherein $R^c$ and $R^d$ each independently represent a hydrogen atom or a monovalent linear or cyclic hydrocarbon group and $R^e$ is a divalent hydrocarbon group.

Some illustrative, non-limiting examples of suitable dihydroxy compounds include those disclosed by name or formula (generic or specific) in U.S. Pat. No. 4,217,438. A nonexclusive list of specific examples of suitable dihydroxy compounds includes the following: resorcinol, 4-bromoresorcinol, hydroquinone, 4,4'-dihydroxybiphenyl, 1,6-dihydroxynaphthalene, 2,6-dihydroxynaphthalene, bis(4-hydroxyphenyl)methane, bis(4-hydroxyphenyl) diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl) phenylmethane, 2,2-bis(4-hydroxy-3-bromophenyl) propane, 1,1-bis(hydroxyphenyl)cyclopentane, 1,1-bis(4-hydroxyphenyl)cyclohexane, 1,1-bis(4-hydroxyphenyl) isobutene, 1,1-bis(4-hydroxyphenyl)cyclododecane, trans-2, 3-bis(4-hydroxyphenyl)-2-butene, 2,2-bis(4-hydroxyphenyl)adamantine, (alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, and the like, as well as combinations comprising at least one of the foregoing.

Polycarbonates may be linear, branched, or a blend of a linear polycarbonate and a branched polycarbonate. The branched polycarbonates may be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents may be added at a level of about 0.05 to about 2.0 wt. %. Branching agents and procedures for making branched polycarbonates are described in U.S. Pat. Nos. 3,635,895 and 4,001,184. All types of polycarbonate end groups are contemplated as being useful in the polycarbonate composition.

In one embodiment, the polycarbonate can be based on bisphenol A, in which each of $A^1$ and $A^2$ is p-phenylene and $Y^1$ is isopropylidene.

Suitable polycarbonates can be manufactured by processes such as interfacial polymerization and melt polymerization. Although the reaction conditions for interfacial polymerization may vary, an exemplary process generally involves dissolving or dispersing a dihydric aromatic reactant, such as BPA, in aqueous caustic soda or potash, adding the resulting mixture to a suitable water-immiscible solvent medium, and contacting the reactants with a carbonate precursor in the presence of a suitable catalyst such as triethylamine or a phase transfer catalyst, and under controlled pH conditions, e.g., about pH 8 to about pH 10. The most commonly used water immiscible solvents include methylene chloride, 1,2-dichloroethane, chlorobenzene, toluene, and the like. Suitable carbonate precursors include, for example, a carbonyl halide such as carbonyl bromide or carbonyl chloride (phosgene), or a haloformate such as a bishaloformates of a dihydric aromatic (e.g., the bischloro-formates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors may also be used.

Among the phase transfer catalysts that may be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-188}$ aryloxy group. Suitable phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, $CH_3[CH_3(CH_2)_2]_3NX$ wherein X is Cl⁻, Br⁻, or a $C_{1-8}$ alkoxy group or $C_{6-188}$ aryloxy group. An effective amount of a phase transfer catalyst may be about 0.1 to about 10 wt. % based on the weight of bisphenol in the phosgenation mixture. In another embodiment an effective amount of phase transfer catalyst may be about 0.5 to about 2 wt. % based on the weight of bisphenol in the phosgenation mixture.

Alternatively, melt processes may be used to make the polycarbonates. Generally, in the melt polymerization process, polycarbonates may be prepared by co-reacting, in a molten state, the dihydroxy reactant(s) and a diaryl carbonate ester, such as diphenyl carbonate, in the presence of a transesterification catalyst. The reaction can be carried out in a number of reaction vessels, typically under progressively deeper vacuum. Volatile monohydric phenol is removed from the molten reactants by distillation and the polymer is isolated as a molten residue.

"Polyestercarbonate, also known as a copolyester-polycarbonate, may also be made using bisphenol A. Such copolymers further contain, in addition to recurring carbonate chain units of the formula (1), repeating units of formula (6)

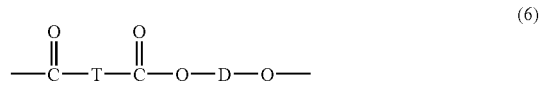

(6)

wherein D is a divalent radical derived from a dihydroxy compound, and may be, for example, a $C_{2-10}$ alkylene radical, a $C_{6-20}$ alicyclic radical, a $C_{6-20}$ aromatic radical or a polyoxyalkylene radical in which the alkylene groups contain 2 to about 6 carbon atoms, specifically 2, 3, or 4 carbon atoms; and T divalent radical derived from a dicarboxylic acid, and may be, for example, a $C_{2-10}$ alkylene radical, a $C_{6-20}$ alicyclic radical, a $C_{6-20}$ alkly aromatic radical, or a $C_{6-20}$ aromatic radical.

In one embodiment, D is a C2–6 alkylene radical. In another embodiment, D is derived from an aromatic dihydroxy compound of formula (7):

(7)

wherein each $R^f$ is independently a halogen atom, a $C_{1-10}$ hydrocarbon group, or a $C_{1-10}$ halogen substituted hydrocarbon group, and n is 0 to 4. The halogen is preferably bromine. Examples of compounds that may be represented by the formula (7) include resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafloro hydroquinone, 2,3,5,6-tetrabromo hydroquinone, or the like; or combinations comprising at least one of the foregoing compounds.

Examples of aromatic dicarboxylic acids that may be used to prepare the polyesters include isophthalic or terephthalic acid, 1,2-di(p-carboxyphenyl)ethane, 4,4'-dicarboxydiphenyl ether, 4,4'-bisbenzoic acid, and mixtures comprising at least one of the foregoing acids. Acids containing fused rings can also be present, such as in 1,4-, 1,5-, or 2,6-naphthalenedicarboxylic acids. Other possible dicarboxylic acids include terephthalic acid, isophthalic acid, naphthalene dicarboxylic acid, cyclohexane dicarboxylic acid, and mixtures comprising at least one of the foregoing acids. A specific dicarboxylic acid comprises a mixture of isophthalic acid and terephthalic acid wherein the weight ratio of terephthalic acid to isophthalic acid is about 10:1 to about 0.2:9.8. In another specific embodiment, D is a $C_{2-6}$ alkylene radical and T is p-phenylene, m-phenylene, naphthalene, a divalent cycloaliphatic radical, and mixtures comprising at least one of the foregoing. This class of polyester includes the poly(alkylene terphthalates).

The copolyester-polycarbonate resins can also prepared by interfacial or melt polymerization technique (see, for example, U.S. Pat. Nos. 3,169,121 and 4,487,896). When using the interfacial polymerization technique, rather than utilizing the dicarboxylic acid per se, it is possible to employ the reactive derivatives of the acid, such as the corresponding acid halides, in particular the acid dichlorides and the acid dibromides. Thus, for example instead of using isophthalic acid, terephthalic acid or mixtures thereof, it is possible to employ isophthaloyl dichloride, terephthaloyl dichloride, and mixtures comprising at least one of the foregoing.

The polycarbonate and polyestercarbonate described above may also be used in combinations with other thermoplastic polymers, for example combinations of polycarbonates and/or polycarbonate copolymers with polyesters. As used herein, a "combination" is inclusive of all mixtures, blends, alloys, and the like. Suitable polyesters comprise repeating units of formula 11, and may be, for example, poly(alkylene dicarboxylates), liquid crystalline polyesters, and polyester copolymers. It is also possible to use a branched polyester in which a branching agent, for example, a glycol having three or more hydroxyl groups or a trifunctional or multifunctional carboxylic acid had been incorporated. Furthermore, it is sometime desirable to have various concentrations of acid and hydroxyl end groups on the polyester, depending on the ultimate end-use of the composition.

Figure 5:
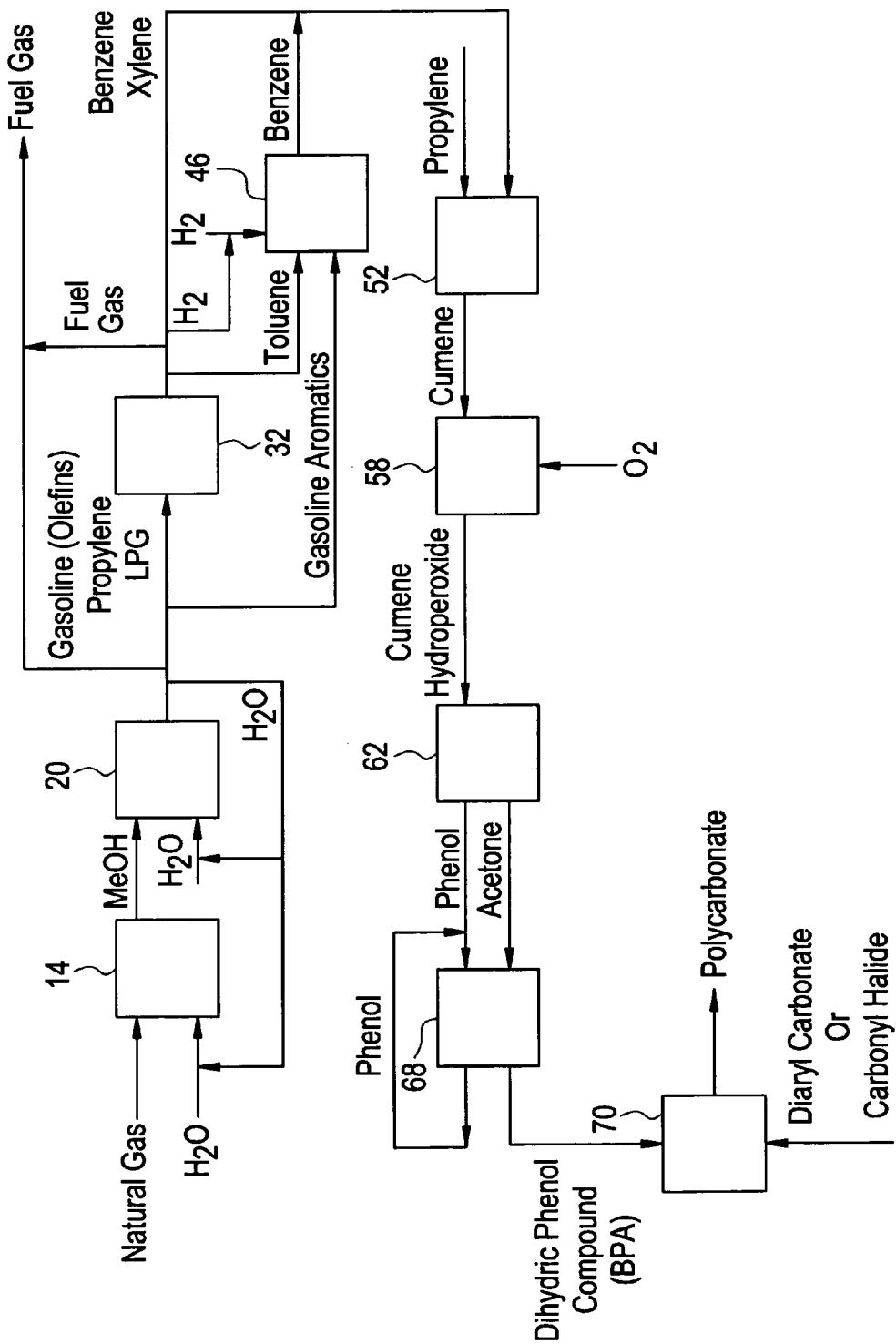
FIG. 5 is a schematic representation of one embodiment of a process for making polycarbonate.

Referring now to FIG. 5, a process for the production of polycabonates comprises combining a methane source (e.g., natural gas) with water in a methane generation process 14 to form methanol. The methanol can be combined with additional water in the production of gasoline (olefins and aromatics), propylene, LPG, fuel gas, and water in a methanol-to-propylene process 20. The gasoline olefins, propylene, and LPG can be reacted in a production-of-aromatics process 32 to form benzene, xylene, toluene, i.e., BTX, hydrogen, and additional fuel gas. Optionally, the toluene and/or xylene, gasoline aromatics, and hydrogen (produced above and/or additional hydrogen) can be reacted in a hydrodealkylation process 46 to form additional benzene. The benzene can then be combined with propylene, optionally including propylene obtained from the methanol-to-propylene process 20, in an alkylation process 52 to form cumene, which is combined with oxygen in an oxidation process 58 to form cumene hydroperoxide. The cumene hydroperoxide can be cleaved in an acidic cleavage process 62 to form the phenol and acetone that are used in a condensation process 68 to produce a dihydric aromatic compound (additional phenol can be added, and the excess phenol can be recycled for reaction with the phenol and acetone from the cleavage process). The dihydric aromatic compound (e.g., BPA) can be reacted 70 with a carbonate precursor (e.g., diaryl carbonate, carbonyl halide, or the like) to form the polycarbonate.

In addition to producing polycarbonate and polyestercarbonate, polyimides can also be produced using the natural gas that is converted to benzene then to the cumene which can be converted to the phenol and acetone. The phenol and acetone are used to form the bisphenol for reaction with a base to form a bisphenol salt that can be reacted with a diamino compound to form a polyimide, e.g., polyetherimide. Thermoplastic polyimides that may be made using bisphenol A or other dihydric aromatic compounds have the general formula (8):

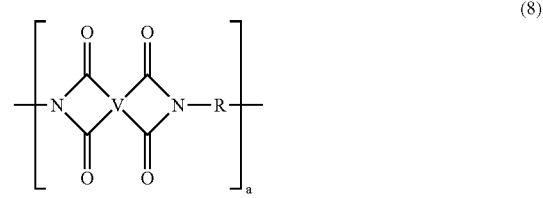

(8)

wherein a is more than 1, typically about 10 to about 1,000 or more, or more specifically about 10 to about 500; and wherein V is a tetravalent linker without limitation, as long as the linker does not impede synthesis or use of the polyimide. Suitable linkers include but are not limited to: (a) substituted or unsubstituted, saturated, unsaturated or aromatic monocyclic and polycyclic groups having about 5 to about 50 carbon atoms, (b) substituted or unsubstituted, linear or branched, saturated or unsaturated alkyl groups having 1 to about 30 carbon atoms; or combinations comprising at least one of the foregoing. Suitable substitutions and/or linkers include, but are not limited to, ethers, epoxides, amides, esters, and combinations comprising at least one of the foregoing. At least a portion of the linkers V must contain a portion derived from a bisphenol. Desirably linkers include but are not limited to tetravalent aromatic radicals of structures (9)

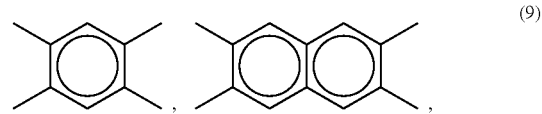

(9)

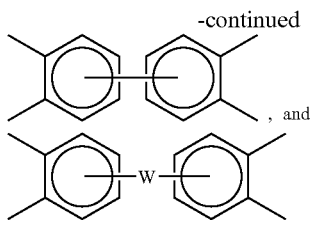
, and wherein W is a divalent moiety selected from the group consisting of —O—, —S—, —C(O)—, —SO$_2$—, —SO—, —C$_y$H$_{2y}$— (y being an integer from 1 to 5), and halogenated derivatives thereof, including perfluoroalkylene groups, or a group of the formula —O-Z-O— wherein the divalent bonds of the —O— or the —O-Z-O— group are in the 3,3', 3,4', 4,3', or the 4,4' positions, and wherein Z includes, but is not limited, to divalent radicals of formulas 10.

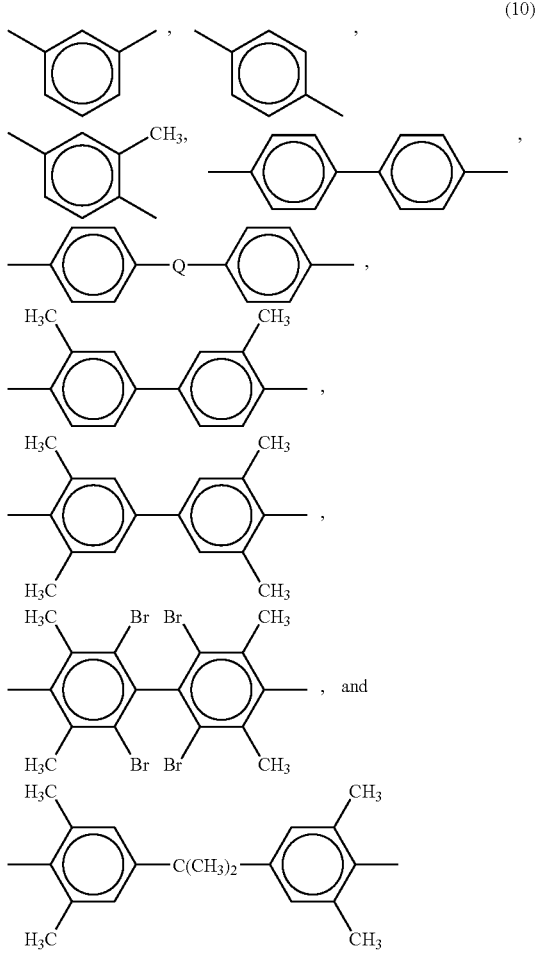

wherein Q includes but is not limited to a divalent moiety selected from the group consisting of —O—, —S—, —C(O)—, —SO$_2$—, —SO—, —C$_y$H$_{2y}$— (y being an integer from 1 to 5), and halogenated derivatives thereof, including perflfluoroalkylene groups.

R in formula (8) includes but is not limited to substituted or unsubstituted divalent organic radicals such as: (a) aromatic hydrocarbon radicals having about 6 to about 20 carbon atoms and halogenated derivatives thereof; (b) straight or branched chain alkylene radicals having about 2 to about 20 carbon atoms; (c) cycloalkylene radicals having about 3 to about 20 carbon atoms, or (d) divalent radicals of the general formula (11)

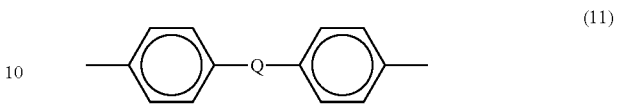

wherein Q includes but is not limited to a divalent moiety selected from the group consisting of —O—, —S—, —C(O)—, —SO$_2$—, —SO—, —C$_y$H$_{2y}$— (y being an integer from 1 to 5), and halogenated derivatives thereof, including perflfluoroalkylene groups.

Exemplary classes of polyimides include polyamidimides and polyetherimides, particularly those polyetherimides which are melt processable, such as those whose preparation and properties are described in U.S. Pat. Nos. 3,803,085 and 3,905,942.

Exemplary polyetherimide resins comprise more than 1, typically about 10 to about 1,000, or more specifically, about 10 to about 500 structural units, of the formula (12)

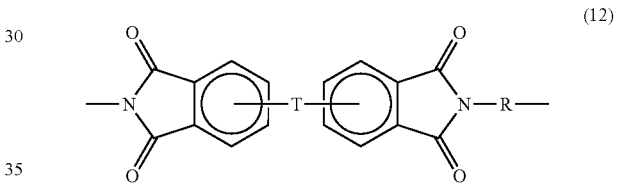

wherein T is —O— or a group of the formula —O-Z-O— wherein the divalent bonds of the —O— or the —O-Z-O— group are in the 3,3', 3,4', 4,3', or the 4,4' positions, and wherein Z includes, but is not limited, to divalent radicals of formula (10) as defined above.

In one embodiment, the polyetherimide may be a copolymer which, in addition to the etherimide units described above, further contains polyimide structural units of the formula (13)

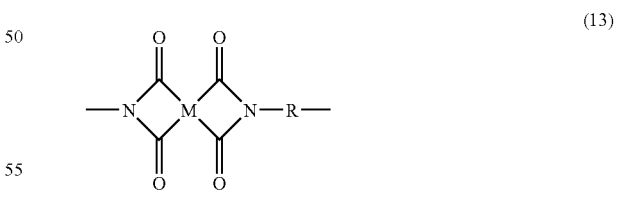

wherein R is as previously defined for formula (8) and M includes, but is not limited to, radicals of formulas (14).

,

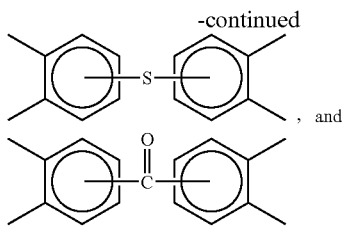

, and

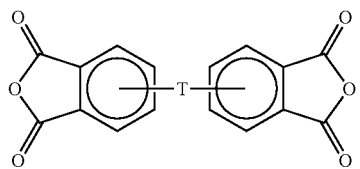

The polyetherimide can be prepared by various methods, including, but not limited to, the reaction of an aromatic bis(ether anhydride) of the formula (15)

(15)

with an organic diamine of the formula (16)

$$H_2N-R-NH_2 \quad (16)$$

wherein R and T are defined in relation to formulas (8) and (12).

Examples of specific aromatic bis(ether anhydride)s and organic diamines are disclosed, for example, in U.S. Pat. Nos. 3,972,902 and 4,455,410. Illustrative examples of aromatic bis(ether anhydride)s of formula (15) include: 2,2-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl] propane dianhydride; 4,4'-bis(2,3-dicarboxyphenoxy)diphenyl ether dianhydride; 4,4'-bis(2,3-dicarboxyphenoxy) diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2, 2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy)benzophenone dianhydride and 4-(2,3-dicarboxyphenoxy)-4'-(3,4-dicarboxyphenoxy)diphenyl sulfone dianhydride, as well as various mixtures comprising at least one of the foregoing.

The bis(ether anhydride)s can be prepared by the hydrolysis, followed by dehydration, of the reaction product of a nitro substituted phenyl dinitrile with a metal salt of a bisphenol compound (e.g., BPA) in the presence of a dipolar, aprotic solvent. An exemplary class of aromatic bis(ether anhydride)s included by formula (15) above includes, but is not limited to, compounds wherein T is of the formula (17):

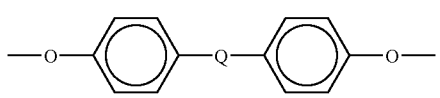
(17)

and the ether linkages, for example, are preferably in the 3,3', 3,4', 4,3', or 4,4' positions, and mixtures comprising at least one of the foregoing, and where Q is as defined above.

Any diamino compound may be employed. Examples of suitable compounds are ethylenediamine, propylenediamine, trimethylenediamine, diethylenetriamine, triethylenetertramine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(b-amino-t-butyl) toluene, bis (p-b-amino-t-butylphenyl) ether, bis(p-b-methyl-o-aminophenyl) benzene, bis(p-b-methyl-o-aminopentyl) benzene, 1,3-diamino-4-isopropylbenzene, bis(4-aminophenyl) sulfide, bis (4-aminophenyl) sulfone, bis(4-aminophenyl) ether and 1,3-bis(3-aminopropyl) tetramethyldisiloxane. Mixtures of these compounds may also be present. Desirably, the diamino compounds are aromatic diamines, especially m- and p-phenylenediamine and mixtures comprising at least one of the foregoing.

In one embodiment, the polyetherimide resin comprises structural units according to formula (12) wherein each R is independently p-phenylene or m-phenylene or a mixture comprising at least one of the foregoing and T is a divalent radical of the formula (18)

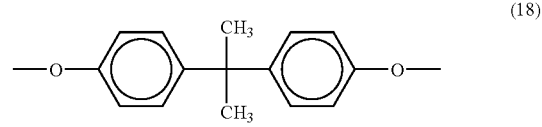
(18)

Included among the many methods of making the polyimides, particularly polyetherimides, are those disclosed in U.S. Pat. Nos. 3,847,867, 3,850,885, 3,852,242, 3,855,178, 3,983,093, and 4,443,591.

In general, the reactions can be carried out employing solvents, e.g., o-dichlorobenzene, m-cresol/toluene and the like, to effect a reaction between the anhydride of formula (15) and the diamine of formula (16), at temperatures of about 100° C. to about 250° C. Alternatively, the polyetherimide can be prepared by melt polymerization of aromatic bis(ether anhydride)s represented by formula (15) and diamines represented by formula (16) by heating a mixture of the starting materials to elevated temperatures with concurrent stirring. Generally, melt polymerizations employ temperatures of about 200° C. to about 400° C. Chain stoppers and branching agents may also be employed in the reaction. When polyetherimide/polyimide copolymers are employed, a dianhydride, such as pyromellitic anhydride, is used in combination with the bis(ether anhydride). The polyetherimide resins can optionally be prepared from reaction of an aromatic bis(ether anhydride) with an organic diamine in which the diamine is present in the reaction mixture at less than or equal to about 0.2 molar excess, and preferably less than or equal to about 0.2 molar excess. Under such conditions the polyetherimide resin may have less than or equal to about 15 microequivalents per gram (μeq/g) acid titratable groups, or, more specifically less than or equal about 10 μeq/g acid titratable groups, as shown by titration with chloroform solution with a solution of 33 weight percent (wt %) hydrobromic acid in glacial acetic acid. Acid-titratable groups are essentially due to amine end-groups in the polyetherimide resin.

One route for the synthesis of polyetherimides proceeds through a bis(4-halophthalimide) having the following structure (19):

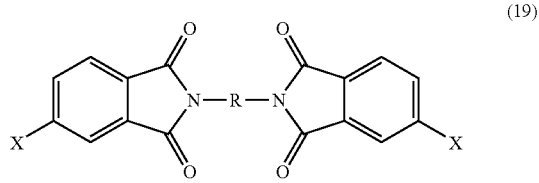

(19)

wherein Y is as described above and X is a halogen. The bis(4-halophthalimide) wherein R is a 1,3-phenyl group (20) is particularly useful.

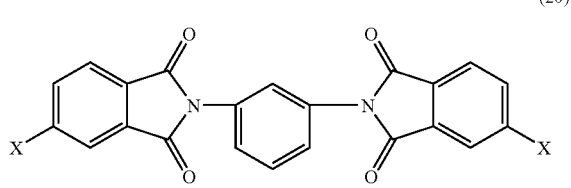

(20)

Bis(halophthalimide)s (19) and (20) are typically formed by the condensation of amines, e.g., 1,3-diaminobenzene with anhydrides, e.g., 4-halophthalic anhydride (21):

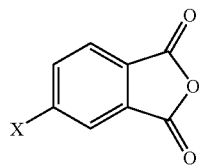

(21)

Polyetherimides may be synthesized by the reaction of the bis(halophthalimide) with an alkali metal salt of a bisphenol such as bisphenol A or a combination of an alkali metal salt of a bisphenol and an alkali metal salt of another dihydroxy substituted aromatic hydrocarbon in the presence or absence of phase transfer catalyst. Suitable phase transfer catalysts are disclosed in U.S. Pat. No. 5,229,482. Suitable dihydroxy substituted aromatic hydrocarbons include those having the formula (22)

OH-A$^3$-OH (22)

wherein A$^3$ is a divalent aromatic hydrocarbon radical. Suitable A$^3$ radicals include m-phenylene, p-phenylene, 4,4'-biphenylene and similar radicals.

Figure 6:
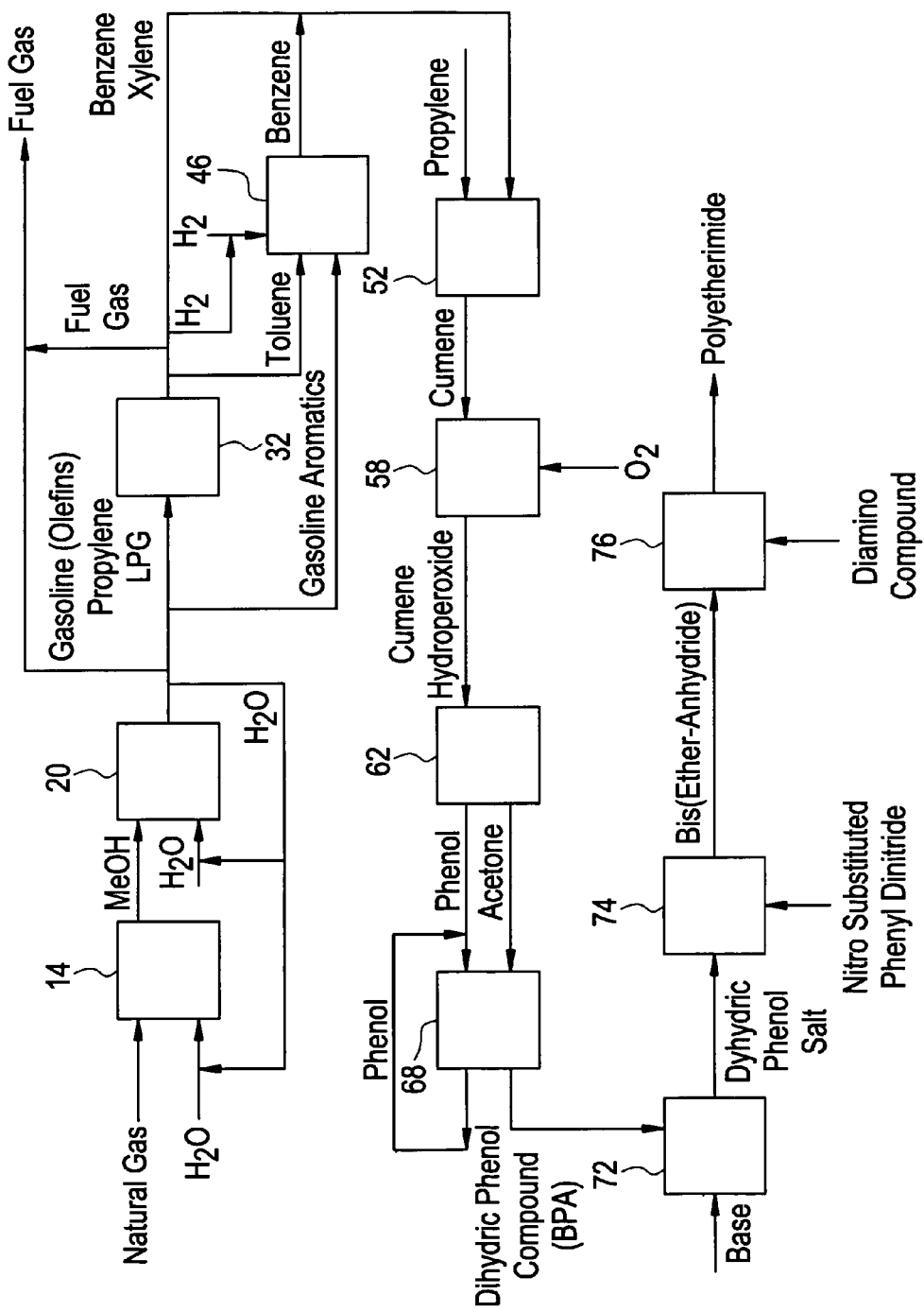
FIG. 6 is a schematic representation of one embodiment of a process for making polyetherimide.

Referring now to FIG. 6, a process for the production of polyetherimide comprises combining a methane source (e.g., natural gas) with water in a methanol generation process 14 to form methanol. The methanol can be combined with additional water in the production of gasoline (olefins and aromatics), propylene, LPG, fuel gas, and water in a methanol-to-propylene process 20. The gasoline olefins, propylene, and LPG can be reacted in a production-of-aromatics process 32 to form benzene, xylene, toluene, i.e., BTX, hydrogen, and additional fuel gas. Optionally, the toluene and/or xylene, gasoline aromatics, and hydrogen (produced above and/or additional hydrogen) can be reacted in a hydrodealkylation process 46 to form additional benzene. The benzene can then be combined with propylene, optionally including propylene obtained from the methanol-to-propylene process 20, in an alkylation process 52 to form cumene, which is combined with oxygen in an oxidation process 58 to form cumene hydroperoxide. The cumene hydroperoxide can be cleaved in an acidic cleavage process 62 to form the phenol and acetone that are used in a condensation process 68 to produce a dihydric aromatic compound (additional phenol can be added, and the excess phenol can be recycled for reaction with the phenol and acetone from the cleavage process). The dihydric aromatic compound (e.g., BPA) can be reacted 72 with a base (e.g., sodium hydroxide) to form a dihydric aromatic salt that can be reacted 74 with a nitro-substitute phenyl dinitride in the formation of bis(ether anhydride). The bis(ether anhydride) can be reacted 76 with a diamino compound to form polyetherimide.

The disclosed processes enable an effective utilization of an otherwise untapped resource (namely natural gas that is flared off), and reduces demand for a commodity that is currently very expensive (e.g., crude oil), while increasing the availability of materials such as benzene. In addition to providing a means for providing benzene, toluene, and xylenes, from a source other than coal or petroleum, the disclosed process provides saving in the production of benzene from methanol by enabling the use of side products from some intermediate steps to be recycled as feedstock into later intermediary steps and/or for use elsewhere in the factory. For example, the gasoline aromatics generated in the production of propylene from methanol can be combined with the toluene produced later in the process to increase the yield of benzene in the hydrodealkylation step. Similarly, the hydrogen generated when the benzene, toluene, and xylenes are produced from the liquefied petroleum gases, propylene and gasoline olefins can be used in the hydrodealkylation step. Additionally, the fuel gas produced during various steps can be used to generate electricity and/or heat for use in this process and/or elsewhere. Thus, the disclosed process for the production of benzene enables the conservation of material and thus reduces costs and waste products in a novel manner. Furthermore, the savings created by combining these processes as described herein carry forward to the products and processes that employ dihydric aromatic compounds such as bisphenol-A. Such processes include the production of plastics, e.g., polycarbonates and polyetherimides, as described above.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for the manufacture of polycarbonate, comprising:
combining methane and inlet water to produce methanol;
converting the methanol to propylene, gasoline aromatics, and gasoline olefins;
converting the propylene and gasoline olefins to hydrogen, first benzene, and toluene;
reacting the first benzene with propylene to form cumene;
reacting the cumene with oxygen to form cumene hydroperoxide;
cleaving the cumene hydroperoxide to produce acetone and phenol;
reacting the phenol and acetone to produce a dihydric aromatic compound; and
reacting the dihydric aromatic compound with a carbonate precursor to form polycarbonate.

2. The method of claim 1, further comprising reacting the toluene, the gasoline aromatics, and hydrogen to produce additional benzene; and reacting the additional benzene with propylene to form cumene.

3. The method of claim 1, further comprising combining outlet water from the production of the methanol with the inlet water.

4. The method of claim 1, comprising reacting the dihydric aromatic compound with a carbonate precursor in an interfacial polymerization reaction.

5. The method of claim 1, wherein the carbonate precursor comprises a diaryl carbonate ester.

6. The method of claim 1, wherein the carbonate precursor comprises a carbonyl halide.

7. The method of claim 6, wherein the carbonyl halide is carbonyl chloride.

8. The method of claim 1, comprising combining natural gas and inlet water to produce methanol.

9. The method of claim 1, wherein the dihydric aromatic compound comprises bisphenol-A.

10. A method for the manufacture of polyetherimide, comprising:
combining methane and water to produce methanol;
converting the methanol to propylene, gasoline aromatics, and gasoline olefins;
converting the propylene and gasoline olefins to hydrogen, first benzene, and toluene;
reacting the first benzene with propylene to form cumene;
reacting the cumene with oxygen to form cumene hydroperoxide;
cleaving the cumene hydroperoxide to produce acetone and phenol;
reacting the phenol and acetone to produce a dihydric aromatic compound;reacting the dihydric aromatic compound with a base to form a dihydric aromatic salt; and
reacting the dihydric aromatic salt with a material to form the polyetherimide.

11. The method of claim 10, wherein reacting the dihydric aromatic salt with the material to form the polyetherimide further comprises reacting the dihydric aromatic salt with a nitro substituted phenyl dinitrile to form a bis(ether anhydride); and
reacting the bis(ether anhydride) with a diamino compound to form polyetherimide.

12. The method of claim 10, wherein the material comprises a bis(halophthalimide).

13. The method of claim 10, further comprising reacting the toluene, the gasoline aromatics, and hydrogen to produce additional benzene; and reacting the additional benzene with propylene to form cumene.

14. The method of claim 10, further comprising combining outlet water from the production of the methanol with the inlet water.

15. The method of claim 10, wherein the dihydric aromatic compound comprises bisphenol-A.

16. A method for the manufacture of cumene, comprising:
combining methane and inlet water to produce methanol;
converting the methanol to propylene, gasoline aromatics, and gasoline olefins;
converting the propylene and gasoline olefins to hydrogen, first benzene, and toluene; and
reacting the first benzene with propylene to form cumene.

17. The method of claim 16, further comprising reacting the toluene, the gasoline aromatics, and hydrogen to produce additional benzene; and combining the additional benzene with the first benzene.

18. The method of claim 16, further comprising combining outlet water from the production of the methanol with the inlet water.

* * * * *